United States Patent [19]

Edwards et al.

[11] Patent Number: 5,224,219
[45] Date of Patent: Jul. 6, 1993

[54] WELDER'S HELMET WITH RETRACTABLE EYE PROTECTIVE LENS AND EASILY REPLACEABLE COVER LENS

[75] Inventors: David B. Edwards; Peter H. Stavros, both of Salt Lake City, Utah

[73] Assignee: Kedman Company, Salt Lake City, Utah

[21] Appl. No.: 751,801

[22] Filed: Aug. 29, 1991

[51] Int. Cl.⁵ .............................. A61F 9/06
[52] U.S. Cl. ........................................ 2/8
[58] Field of Search ............... 2/8, 9, 10, 441, 424; 219/147

[56] References Cited

U.S. PATENT DOCUMENTS

| | | | |
|---|---|---|---|
| 1,205,308 | 11/1916 | Work | 2/8 |
| 2,277,090 | 3/1942 | Feiler | 2/8 |
| 2,726,395 | 12/1955 | Anderson | 2/8 |
| 3,444,561 | 5/1969 | Boyer | 2/8 |
| 3,768,099 | 10/1973 | Manz | 2/8 |
| 5,012,528 | 5/1991 | Pernicka et al. | 2/8 X |

Primary Examiner—Peter Nerbun
Attorney, Agent, or Firm—Mallinckrodt & Mallinckrodt

[57] ABSTRACT

A welder's helmet having a face-protective shell adapted for wearing over the face of a welder during welding operations, the shell having a front wall provided with a sight opening therethrough and rearwardly extending walls including top, bottom, and side walls, peripheral to the front wall for enclosing the face of a welder is provided. The helmet features a retractable carrier frame for a light-filtering lens normally in a position framing the sight opening and movable upwardly and backwardly to a position substantially coplanar with and substantially entirely within the area of the top wall of the face protective shell of the helmet and vice versa, guide means for the aforesaid movement of the carrier frame, and actuator means enabling a welder wearing the helmet to carry out the movement of the carrier frame. Also provided is an easily replaceable protective cover lens. Included is protective cover lens assembly comprising a cover lens; and a cover lens carrier frame having a side opening for the insertion of said cover lens. The cover lens assembly is slidably inserted in an opening in an outer frame at the outside face of the front wall of the helmet shell and disposed peripherally of the sight opening.

15 Claims, 4 Drawing Sheets

WELDER'S HELMET WITH RETRACTABLE EYE PROTECTIVE LENS AND EASILY REPLACEABLE COVER LENS

BACKGROUND OF THE INVENTION

1. Field

The invention is in the field of protective helmets for welders wherein lenses are provided, one being an eye-protective lens mounted for movement into and away from the welder's line of sight and another as a cover for the first one.

2. State of the Art

Most welding helmets in use today have a fixed, light-filtering lens mounted therein, the helmet itself being pivotally mounted on a headband so that the entire helmet can be pivoted upwardly over the head of a welder when he is not actually welding, thereby enabling the welder to see without the light-filtering lens. While this is common current practice, the face and eyes of the welder are left unprotected when the helmet is raised, except for protective eyewear that may be (but is usually not) worn by the welder beneath his or her helmet.

Various constructions for a welder's helmet with a light-filtering lens, which, itself, can be conveniently moved out of and back into the line of vision to thereby leave the helmet in place in front of the welder's face, have been proposed in the past. Some have also included a clear but protective cover lens to protect the welder's face and eyes when the light-filtering lens is moved out of the way and to provide a cover for the light-filtering lens. Helmets which merely pivotally mount the light-filtering lens at its top so that a welder can pivot such lens up and out of the way, leave this lens projecting undesirably outwardly from the face of the helmet.

Reference is made to Manz U.S. Pat. No. 3,768,099, issued Oct. 30, 1973, which provides a light-filtering lens within a carrier frame that is slidable upwardly and downwardly in an fixed frame at the inside front wall of the face-protective shell of a welder's helmet. Such front wall has a sight opening covered by the light-filtering lens in the down position of the carrier frame. However, the size of such lens is limited by the clearance space that exists from the upper margin of the sight opening to the top wall of the helmet shell. With the stationary frame providing a track for the movable carrier frame, backward movement of such carrier frame is restricted as it moves upwardly until it has moved upwardly sufficiently far to be substantially clear of the track but so that its lower margin will pivot therein for backward movement.

Since the carrier frame incorporating the light-filtering lens of this Manz patent has to nearly clear the stationary frame before backward movement is possible and since overhead clearance is limited due to the proximity of the top of the helmet shell, the size of the eye-protective lens is limited. A carrier frame for a relatively large light-filtering lens will not clear the top and sides of the stationary frame for effective backward movement, nor will it fit into a retracted position upwardly of the sight opening at the front of the helmet shell. This is because such retracted position is solely behind the front face of the helmet shell. Restriction against backward movement of the carrier frame does not allow for its retraction under the top of the helmet shell.

A welder's helmet having a retractable lens of large size has long been desired, but providing for same has remained a problem. Even though U.S. Pat. No. 4,853,973 of Boochard apparently provides a helmet with a large lens, the front or visor portion of the helmet shell is a separable part thereof and is pivotally mounted so as to move up and out of the way, leaving the welder a clear and unobstructed view through a clear protective lens, which remains in place. The pivotal arrangement is complicated, and the pivoted portion of the welder's helmet projects beyond the remainder of the helmet when raised and interferes with movement in tight spots.

SUMMARY OF THE INVENTION

A principle objective in the making of the present invention was to provide a welder's helmet with a retractable carrier frame for a light-filtering lens, said carrier frame arranged to accommodate various types of standard light-filtering lenses of desired large size and that will not interfere with the welder's work. Another objective was to provide a welder's helmet with an easily replaceable cover lens.

In accordance with the invention, there is provided a welder's helmet having a face-protective shell adapted for wearing over the face of a welder during welding operations, said shell having a front wall provided with a sight opening therethrough and rearwardly extending walls including top, bottom, and side walls, peripheral to said front wall for enclosing the face of the welder. The helmet accommodates a retractable carrier frame arranged for retraction upwardly and rearwardly from a normal position within the welder's line of sight to a retracted position that is out-of-the-way under the top of the helmet shell and that is also arranged for return movement along a path extending forwardly and downwardly.

The instant invention enables retraction of the light-filtering lens to a position away from the front of and under the top of the helmet shell and is, thus, unlike prior designs which only move such a lens upwardly and downwardly behind the front face of the helmet shell. Guiding such movement is an inner frame at the inside face of the front wall of the helmet shell and disposed peripherally of the sight opening, such retractable carrier frame having means slidably received by the inner frame. Such inner frame is a separately molded piece equipped with a flange for attachment around the sight opening or, preferably, is simply molded as a portion of the helmet shell.

There is also preferably provided a cover lens assembly including a cover lens mounted in a cover lens carrier frame, such carrier frame being fashioned for insertion into a stationary, outer frame. The outer frame is disposed at the outside of the front wall of the helmet shell and peripherally of the sight opening therethrough such frame is either attached to the outside of the helmet surrounding the sight opening, or, again, is provided by simply molding as a portion of the helmet shell.

THE DRAWINGS

The best mode presently contemplated for carrying out the invention commercially is illustrated in the accompanying drawings, in which:

FIG. 1 is a perspective view looking toward the top, bottom, front and one side of a welder's helmet embodying the invention;

FIG. 2, an exploded view showing in front elevation the separate elements comprising the carrier frame and cover-lens assembly;

FIG. 3, a vertical section taken along line 3—3 of FIG. 1 and drawn to a larger scale;

FIG. 4 a fragmentary view taken along line 4—4 of FIG. 3 and showing in elevation the inside of the helmet, the light-filtering lens being in its down position;

FIG. 5, a fragmentary view taken along line 5—5 of FIG. 3 and showing in inside elevation the upper wall of the helmet, the light-filtering lens being shown in its down position;

FIG. 6, a fragmentary, transverse, vertical section taken along line 6—6 of FIG. 3 and showing the actuator mechanism at the top of the helmet;

FIG. 7, a fragmentary, transverse, vertical section taken along line 7—7 of FIG. 4 showing the arrangement of both the cover and light-filtering lens assemblies;

FIG. 8, a fragmentary, horizontal section taken along line 8—8 of FIG. 6 to show the inside of the actuator housing with the actuator in the up position;

FIG. 9, a view corresponding to that of FIG. 8 but showing the actuator in the half-down position;

FIG. 10, a fragmentary view largely similar to that of FIG. 3, but showing the retractable carrier frame and light-filtering lens in their up position;

FIG. 11, a view corresponding to that of FIG. 10, but showing the retractable carrier frame and light-filtering lens in their half-up position; and FIG. 12, a fragmentary vertical section taken along line 12—12 of FIG. 1.

DETAILED DESCRIPTION OF THE ILLUSTRATED EMBODIMENT

Figure 1:
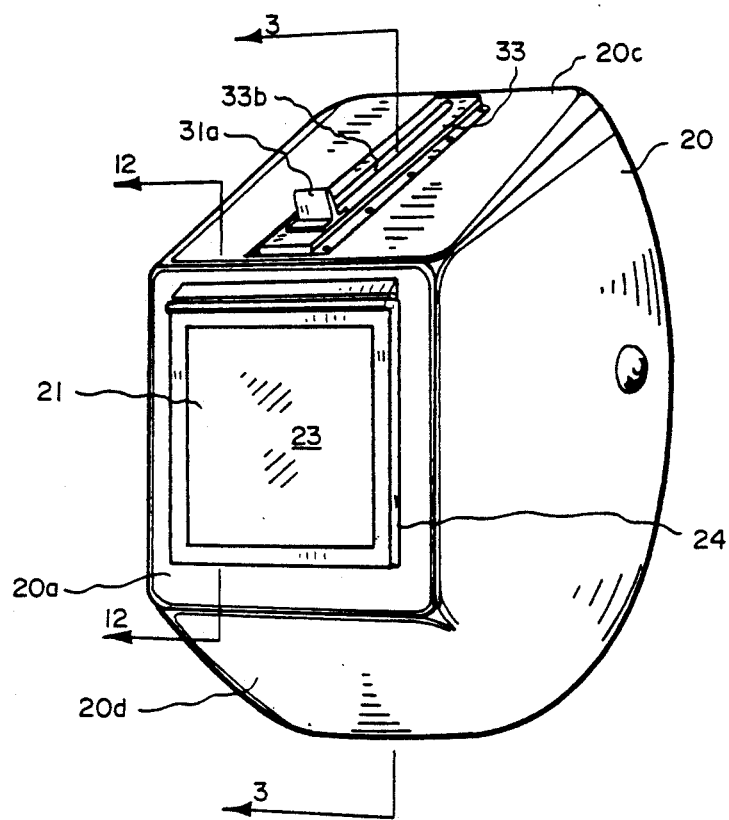
Figures 3, 12:
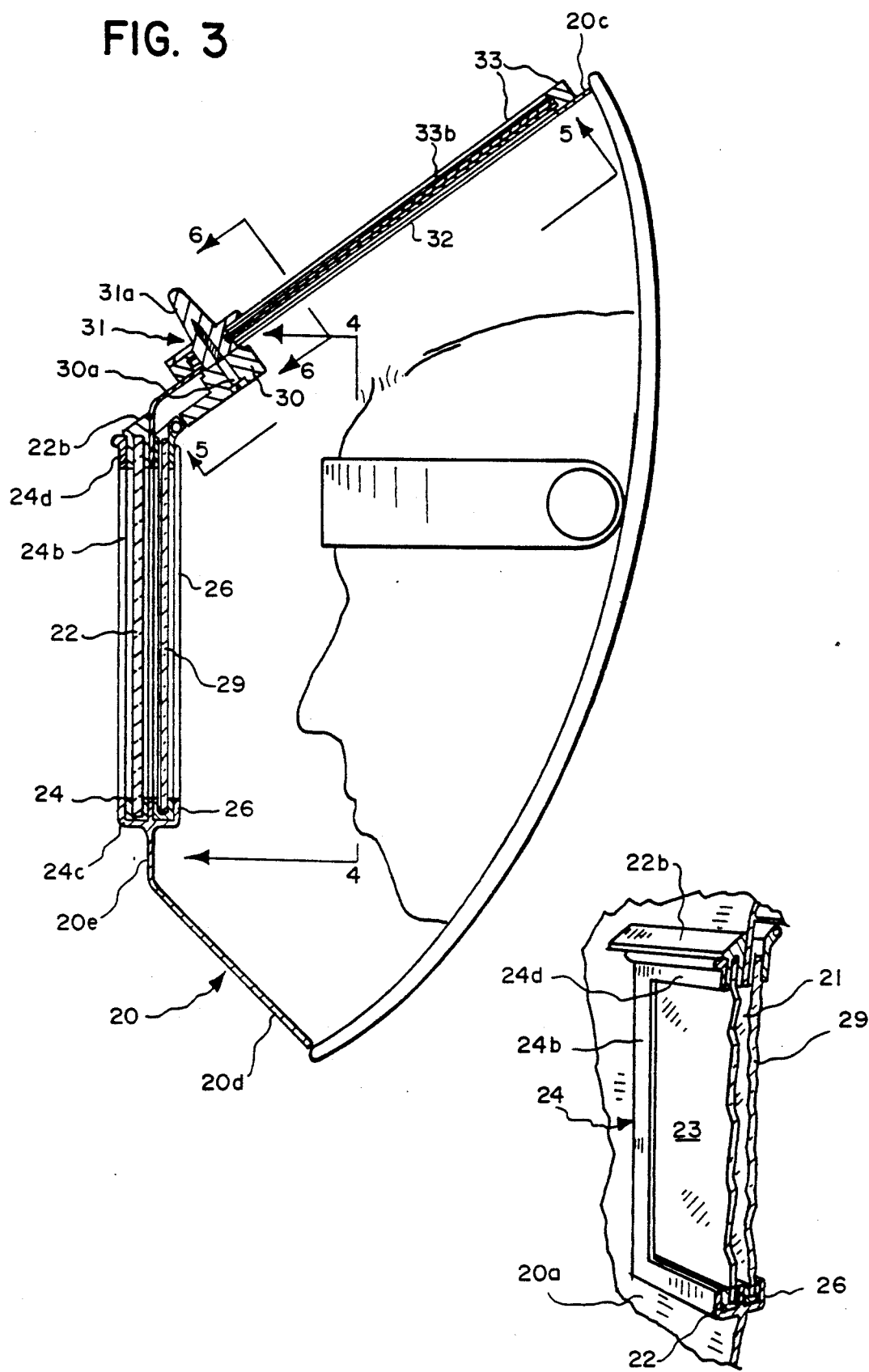

As illustrated in FIG. 1, a welder's helmet of usual construction has a shell 20 which includes a front wall 20a, and, peripherally thereof, two divergent side walls (only one of which 20b is shown), a top wall 20c, and a bottom wall 20d. A sight opening 21, FIG. 12, is provided in front wall 20a.

Figure 2:
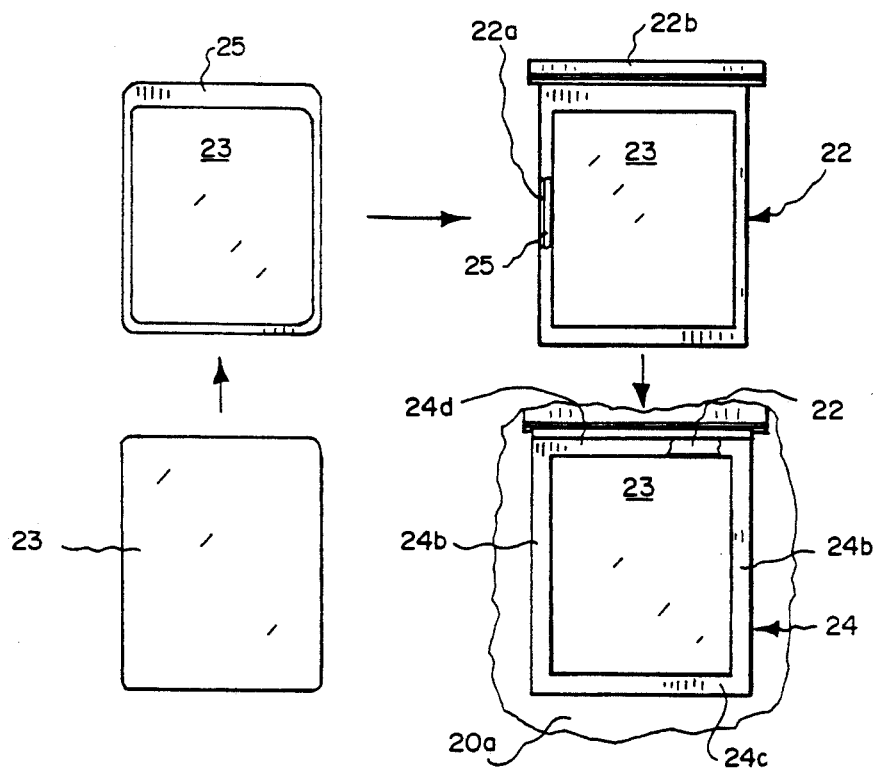
Figure 7:
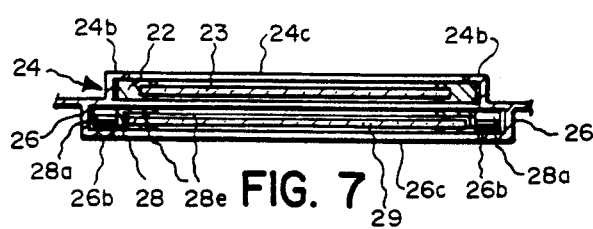

As indicated in FIG. 2, cover lens frame 22 for a clear cover lens 23 is removably placed in a stationary, outer frame 24, comprised of opposite frame members 24b, respectively, bottom frame member 24c, and top frame member 24d. These frame members are disposed at the outer face of front wall 20a of helmet shell 20 around sight opening 21. Cover lens 23 is fitted into its carrier frame 22 through a slot 22a formed in a side member of such cover lens frame 22. In turn, such cover lens carrier frame 22 slides into outer frame 24 through a slot formed in its top frame member 24d and fits snugly therein as shown in FIG. 7. The top of cover lens carrier frame 22 is sloped outwardly at 22b, FIG. 12, so as not to permit the accumulation of debris. With cover lens 23 pressed up against the outside rails of its carrier frame 22 and with such carrier frame 22 fitted snugly into outer frame 24, there is no means of entry for debris or a place for debris to collect.

Cover lens may be and preferably is of a standard large size whose thickness is great enough to fit snugly into cover lens carrier frame 22. However, since some large lenses are thinner, they can be held snugly in position by installation of an optional, bent, rectangular, flat spring 25, FIG. 2, of window formation as a filler for the grooves in carrier frame 22 that receive and hold cover lens 23.

As an alternative embodiment, the cover lens carrier frame 22 with a light-filtering lens instead of a clear lens could stand alone as in the usual welding helmets of the prior art which merely pivots on a headband where the lens is inconveniently mounted from the inside of the helmet shell and is difficult to replace. Such stand alone lens carrier frame would allow for easy replacement of the lens.

In the illustrated embodiment, outer frame 24 is molded directly in helmet shell 20 as grooves at opposite sides and at the bottom of sight opening 21 and as an open slot along the top, but it can be a separate frame attached by cement or by fastening means such as rivets.

An inner frame 26 is provided at the inside face of front wall 20a of helmet shell 20 and is disposed peripherally of sight opening 21. It may be and preferably is molded into shell 20, FIGS. 3, 7, and 12, in helmet shell 20 see. As shown in FIG. 7, inner frame 26 includes opposite frame members 26b, respectively, defining grooves and a bottom frame member 26c, defining grooves for receiving a rectangular, retractable carrier frame 28, for a light-filtering lens 29, FIG. 4. Such carrier frame 28 has slideway grooves on at least three sides and is open at the top to provide for insertion of light-filtering lens 29. Advantageously, the front frame members of carrier frame 28 have a preferably continuous ridge 28e, FIG. 7, shown in FIG. 7, running along their inside faces longitudinally thereof.

Figure 4:
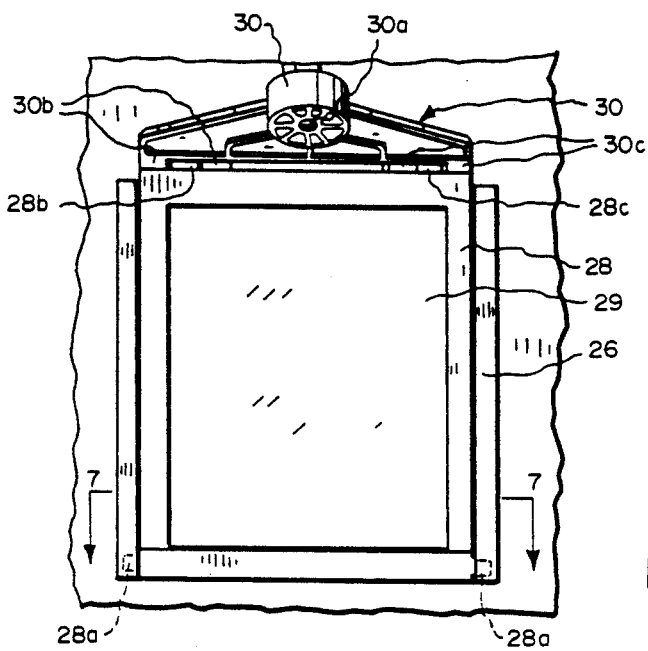
Figure 10:
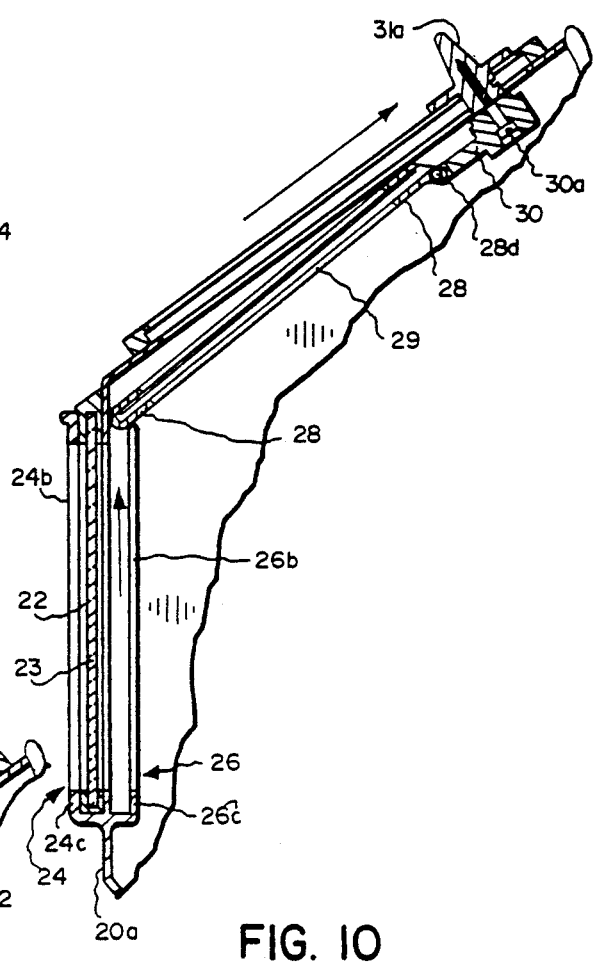
Figure 11:
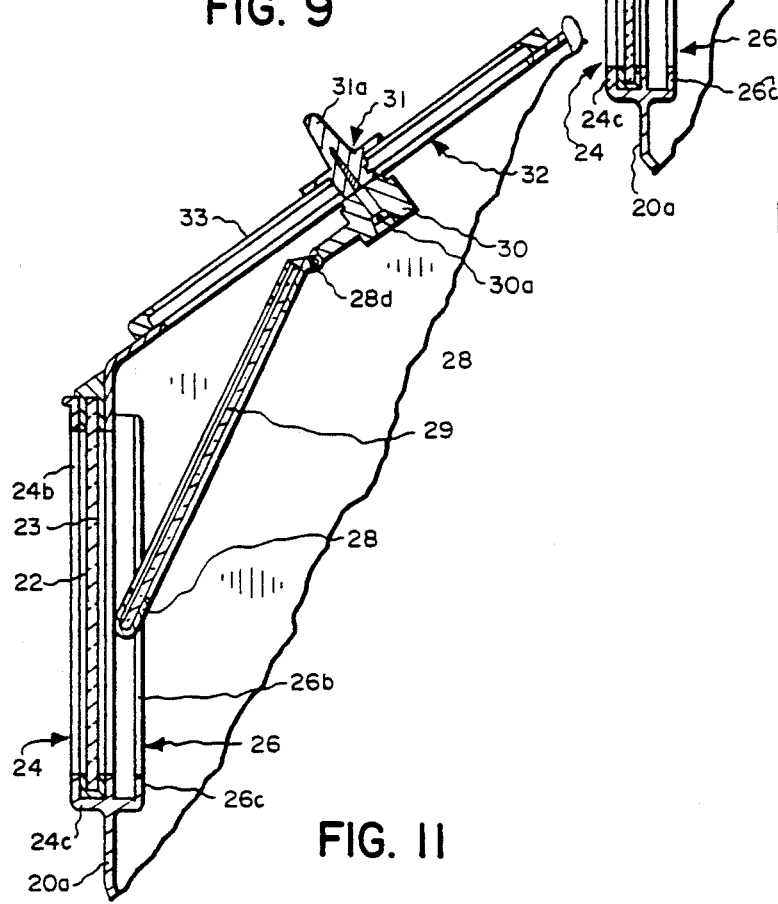

Retractable carrier frame 28 is slidably fitted into grooves 26b of inner frame 26 at two discreet points by means of cylindrical pivot pins 28a, FIGS. 4 and 7, for upward and backward movement in raising light filtering lens 29 to a position under the top of helmet 20, see FIG. 10, out of the line of sight and for downward and forward movements as in FIG. 11 back to the welding position of FIG. 3. In order to slide freely, the diameter of the pivots should be slightly less than the width of the groove or track into which they go. For example, the pivot might be 0.18 inches in diameter and the receiving groove of frame 26 0.30 inches in width. In the down position, the bottom member of retractable carrier frame 28 fits snugly into bottom groove 26c with pivot pins 28a extending into side grooves 26b. As so fitted into the grooves of inner frame 26, retractable carrier frame 28 serves to seal against the inadvertent entry of harmful ray from the welding operation other than through lens 29.

Aforementioned pivot pins 28a of retractable carrier frame 28 extend out from the sides of frame 28 thus providing for receipt of said frame 28 by inner frame 26 at two discreet points. Thereby frame 28 is enabled to move backwardly to a position under the top wall 20c of the helmet without first having cleared inner frame 26. Consequently, the retractable carrier frame can accommodate a much larger lens than sliding windows of the prior art. The accommodation of a larger lens is desired because of the greater visibility allowed. The device of the invention accommodates standard large size lenses commonly sold in the trade for use with prior art welding helmets of much less desirable construction.

Figure 5:
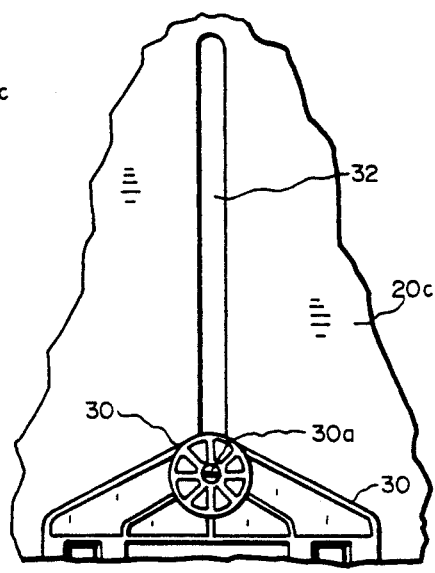
Figure 6:
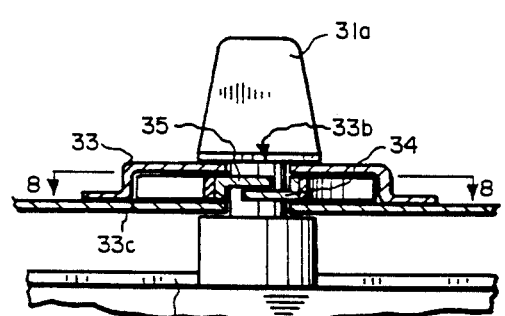

Means for manually raising and lowering the retractable carrier frame is preferably provided by linking an actuator to retractable carrier frame 28 by interconnecting yoke 30, FIGS. 3, 4, and 6. Retractable carrier frame 28 also has special means for attaching to yoke 30. In the form illustrated, the lower end of yoke 30 is attached by hinge means 20, FIGS. 4–6, to carrier frame 28. Preferably formed as a portion of retractable carrier frame 28, a lower hinge arrangement includes the following: the upper end of carrier frame 28 is angled back and, offset from either end, lower hinge elements 28b and 28c are formed respectively. Corresponding upper hinge elements, 30b and 30c, are disposed at either side of the lower edge of yoke 30, FIG. 4, for pivotally interengaging said pair of lower hinge elements. Said hinge elements have a hole therethrough for receiving hinge pin 28d, FIGS. 10 and 11.

Figure 9:
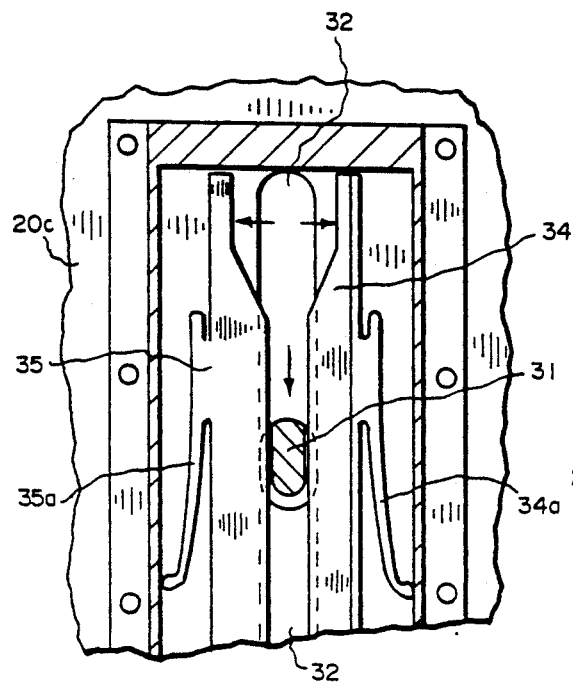

At its upper end, yoke 30 is abutted against and attached to actuator 31, as shown in FIGS. 3 and 6, by means of screw 30a, FIGS. 9 and 10. It is here that actuator 31 passes through slot 32, FIGS. 5 and 9, of helmet 20 into slideway 33, FIGS. 1, 6 and 11 for housing the lower part of the actuator assembly. Slideway 33 is elongate and secured to the exterior face of top wall 20c of helmet 20 as by means of rivets. Actuator 31 has an upstanding knob 31a, FIGS. 6, 10, and 11, that can be easily grasped while wearing heavy welding gloves to retract lens 29 out of the line of sight or return it to the welding position.

Figure 8:
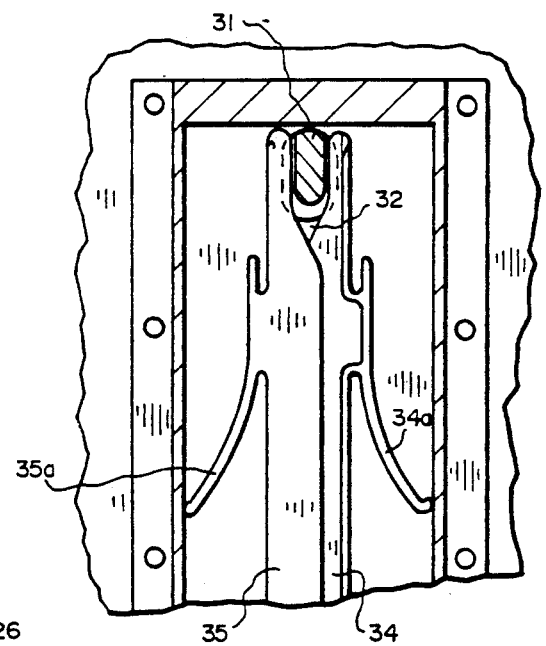

Slideway 33 is preferably molded from thermoplastic material, so as to have an open interior 33a, FIG. 6, below elongate actuator-receiving slot 33b, FIG. 1, and above corresponding slot 32 of helmet 20, within open interior 33a of slideway 33, in parallel with slots 33b and 32, is the actuator assembly comprising a pair of normally overlapped, elongate scissor leaves 34 and 35, respectively, FIG. 8, having formed at opposite ends thereof leaf springs, 34a and 35a, to thereby provide resistance counter to the force exerted against knob 31a of actuator 31 by the welder and thereby hold the actuator and lens frame 28 in position when counter force is not exerted. Moreover, such leaf springs in the down position of lens frame 28 urge such frame against inner frame 26 to prevent the inadvertent entry of harmful light rays. In this manner the combination scissor leaves and leaf springs provide resilient means normally urging retractable carrier frame 28 toward inner frame 26 while such frame is in its down position. Although said resilient means so urges, it is yieldable to permit movement of retractable carrier frame 28 inwardly of the helmet as it is being raised It should be noted that entry of debris through slots 33b and 32 is prevented by the overlapped scissor leaves 34 and 35.

Whereas this invention is here illustrated and described with reference to an embodiment thereof presently contemplated as the best mode of carrying out such invention in actual practice, it is to be understood that various changes may be made in adapting the invention to different embodiments without departing from the broader inventive concepts disclosed herein and comprehended by the claims that follow.

We claim:

1. A welder's helmet, comprising:
   a face-protective shell adapted for wearing over the face of a welder during welding operations, said shell having a front wall provided with a sight opening therethrough and rearwardly extending walls including top, bottom, and side walls, peripheral to said front wall for enclosing the face of the welder;
   a retractable carrier frame for a light-filtering lens normally in a position framing said sight opening and movable upwardly and backwardly to a position substantially coplanar with and substantially entirely within the area of said top wall of the face protective shell of the helmet and vice versa;
   guide means for the aforesaid movement of said carrier frame, said guide means comprising means defining similarly oriented, up and down grooves fastened to said shell at opposite lateral sides of and extending substantially from the bottom of said carrier frame in its down position to substantially said top wall of the shell, and pivot means fastened to said carrier frame adjacent to the lower end thereof and projecting therefrom into said grooves, respectively, the upper portion of said carrier frame being free to move backwardly within said shell and about said pivot means as centers as said carrie frame is moved upwardly relative to said shell;
   and actuator means enabling a welder wearing said helmet to carry out said movement of the carrier frame, said actuator means comprising an actuating member connected to the upper end of said carrier frame, and guide means for said actuating member extending backwardly of said top wall of the shell for guiding movement of said actuating means as it is moved backwardly of said top wall of the shell to move said carrier frame upwardly to its up position under the top of the helmet, and as said actuating means is moved forwardly to move the carrier frame from its said up position to its down position over the sight opening.

2. A welder's helmet according to claim 1, wherein the retractable carrier frame is of overall size approaching that of the front wall of the face-protective shell of the helmet so as to receive a very large light-filtering lens.

3. A welder's helmet according to claim 1, comprising resilient means normally urging said retractable carrier frame toward said inner frame but yieldable to permit movement of said retractable carrier frame inwardly of the helmet as it is being raised.

4. A welder's helmet, comprising:
   a face-protective shell adapted for wearing over the face of a welder during welding operations, said shell having a front wall provided with a sight opening therethrough and rearwardly extending walls including top, bottom, and side walls, peripheral to said front wall for enclosing the face of the welder;
   a retractable carrier frame for a light-filtering lens normally in a position framing said sight opening and movable upwardly and backwardly to a position substantially coplanar with and substantially entirely within the area of said top wall of the face protective shell of the helmet and vice versa, said retractable carrier frame being rectangular and having slideway grooves at three sides thereof and an open slot in the fourth side into which the light-filtering lens is inserted;
   guide means for the aforesaid movement of said carrier frame; and
   actuator means enabling a welder wearing said helmet to carry out said movement of the carrier frame.

5. A welder's helmet according to claim 1, wherein the actuator means is attached at its lower end to the upper end of a stiff yoke and said yoke is pivotally attached at its lower end to said retractable carrier frame.

6. A welder's helmet according to claim 1, further comprising:

an inner frame at the inside face of the front wall of the helmet shell and disposed peripherally of the sight opening along its side and bottom edges to provide the up and down grooves, the retractable carrier frame being slid within said inner frame for up and down movement therein relative to the sight opening so said retractable carrier frame and light-filtering lens will rest under the top wall of the helmet shell when moved upwardly away from the sight opening, the retractable carrier frame in its down position abutting said inner frame for sealing against the inadvertent entry into the helmet of rays from a welding operation.

7. A welder's helmet according to claim 6, wherein the inner frame is provided by grooves at the sides and bottom of the inside face of the front wall of the helmet shell which peripherally define the sight opening.

8. A welder's helmet, comprising, a face-protective shell adapted for wearing over the face of a welder during welding operations, said shell having a front wall provided with a sight opening therethrough and rearwardly extending walls including top, bottom, and side walls, peripheral to said front wall for enclosing the face of the welder;

a retractable carrier frame for a light-filtering lens normally in a position framing said sight opening and movable upwardly and backwardly to a position substantially coplanar with and substantially entirely within the area of said top wall of the face protective shell of the helmet and vice versa;

guide means for the aforesaid movement of said carrier frame;

actuator means enabling a welder wearing said helmet to carry out said movement of the carrier frame: and an inner frame at the inside face of the front wall of the helmet shell and disposed peripherally of the sight opening along its side and bottom edges, the retractable carrier frame having means slidably received at two points by said inner frame for up and down movement therein relative to the sight opening so the retractable carrier frame and light-filtering lens will rest under the top wall of the helmet shell when moved upwardly away from the sight opening, the retractable carrier frame in its down position abutting said inner frame for sealing against the inadvertent entry into the helmet of rays from a welding operation, the means of the retractable carrier frame that are slidably received by said inner frame at two points being a cylindrical pivot pin near the bottom of each side received by corresponding grooves of the inner frame for guiding the retractable carrier frame from its down position over the sight opening to an up position under the top of the helmet and vice versa.

9. A welder's helmet according to claim 1, including an easily replaceable protective cover lens assembly.

10. A welder's helmet according to claim 9, wherein the protective cover lens assembly includes a cover lens; a cover lens carrier frame having a side opening for the insertion of said cover lens; and an outer frame at the outside face of the front wall of the helmet shell and disposed peripherally of the sight opening with an opening for the insertion of said cover lens carrier frame.

11. A welder's helmet, comprising:

a face-protective shell adapted for wearing over the face of a welder during welding operations, said shell having a front wall provided with a sight opening therethrough and rearwardly extending walls including top, bottom, and side walls, peripheral to said front wall for enclosing the face of the welder;

a retractable carrier frame for a light-filtering lens normally in a position framing said sight opening and movable upwardly and backwardly to a position substantially coplanar with and substantially entirely within the area of said top wall of the face protective shell of the helmet and vice versa;

guide means for the aforesaid movement of said carrier frame;

actuator means enabling a welder wearing said helmet to carry out said movement of the carrier frame; and an easily replaceable protective cover lens assembly including a cover lens; a cover lens carrier frame having a side opening for the insertion of said cover lens; and an outer frame at the outside face of the front wall of the helmet shell and disposed peripherally of the sight opening with an opening for the insertion of said cover lens carrier frame, the opening in the outer frame for the insertion of the cover lens assembly being along the upper edge of the outer frame, and the upper edge of said cover lens carrier frame being sloped so as not to catch debris from welding operations when inserted into said opening.

12. A welder's helmet comprising:

a face-protective shell adapted for wearing over the face of a welder during welding operations, said shell having a front wall provided with a sight opening therethrough, rearwardly extending peripheral walls including a top wall provided with an elongate slot therethrough extending from front to back thereof, and side walls for enclosing the face of the welder;

an outer frame at the outside face of the front wall of the helmet shell and disposed peripherally of said sight opening, said outer frame having an opening for slidably receiving a cover lens assembly;

an inner frame at the inside face of the front wall of the helmet shell and disposed peripherally of said sight opening along its side and bottom edges for slidably interengaging a retractable lens carrier frame;

a cover lens assembly including a cover lens carrier frame having an opening along one side for the insertion of a cover lens and a sloped upper edge so as not to catch debris from welding operations, and a cover lens slidably mounted in said cover lens carrier frame; and a light-filtering lens;

actuator assembly means for retractably mounting said light-filtering lens and comprising:

an actuator having an actuator knob for manually moving the retractable lens carrier frame;

an actuator housing having therein a pair of combination leaf spring and scissor leaves for urging said light-filtering lens to remain in the up or down position, whereby in the down position the actuator assembly urges the carrier frame against the inner frame and seals against the penetration of light around the edges of the carrier frame and effectively seals the housing against entry of debris;

a retractable lens carrier frame having formed at its bottom outside edges a pair of cylindrical pivots, the upper border of said carrier frame forming a pair of lower hinge pieces;

a yoke having corresponding upper hinge elements disposed at opposite sides, respectively, of its lower edge for pivotally interengaging said pair of lower hinge elements of said light-filtering lens carrier frame, and having a hole therethrough for receiving a hinge pin and having at its upper end a surface for abutting against and attaching to said actuator;

means for attaching said actuator to said yoke; and a hinge pin for pivotally connecting said yoke to said retractable lens carrier frame.

13. A welder's helmet according to claim 12, wherein the lenses are of standard large size.

14. A welder's helmet according to claim 1, wherein the sight opening is normally covered by a clear, protective, lens, said clear, protective lens being inserted in a carrier frame with a side opening for the snug insertion thereof;

and wherein there is a frame on the outer front face of said helmet peripherally of said sight opening with its top open for removal and replacement of said clear, protective, lens and having frame members on the side and bottom edges of said sight opening for slidably receiving said carrier frame.

15. A welder's helmet according to claim 14, wherein the sight opening is of sufficient dimension to accommodate a lens of standard large size.

* * * * *